United States Patent [19]

Lui

[11] Patent Number: 5,739,394
[45] Date of Patent: Apr. 14, 1998

[54] 3,3-DIOXY-4,4,4-TRIFLUOROBUTYRIC ACID DERIVATIVES

[75] Inventor: Norbert Lui, Köln, Germany

[73] Assignee: Bayer Aktiengesellschaft, Leverkusen, Germany

[21] Appl. No.: 767,581

[22] Filed: Dec. 16, 1996

[30] Foreign Application Priority Data

Dec. 22, 1995 [DE] Germany ............... 195 48 416.9

[51] Int. Cl.[6] .................................................. C07C 59/00
[52] U.S. Cl. .................... 562/586; 560/184; 568/397; 568/596; 568/597; 568/598; 568/600
[58] Field of Search ............. 549/549; 560/184; 562/586; 568/397, 596, 597, 598, 600

[56] References Cited

U.S. PATENT DOCUMENTS 5,093,532  3/1992  Baasner et al. ........................ 568/407

FOREIGN PATENT DOCUMENTS 0371950  6/1990  European Pat. Off. .
0491137  6/1992  European Pat. Off. .
0625516  11/1994  European Pat. Off. .
4025188  2/1992  Germany .

OTHER PUBLICATIONS

Journal of the American Chemical Society, Bd. 75, Nr. 13, Jul. 5, 1953, Seiten 3152–3153, XP000652734 Mcbee, E.T., et al., "The Preparation and Reactions of Fluorine–Containing Acetoacetic Esters", *Tabelle 1*.
Database Crossfire, Beilstein BRN 1373760, XP002029001 & J. Org. Chem. USSR, Bd. 15, 1979, Seite 627 Kondratenko, et al.: & J. Fluorine Chem., Bd. 57, 1992, Seiten 177–190, Yamanaka, et al.
Database Crossfire, Beilstein BRN 1377272, XP002029002 & J. Org. Chem. USSR, Bd. 15, 1979, Seite 627, Kondratenko, et al.: & J. Fluorine Chem., Bd. 44, 1989, Seiten 377–394, Aubert, et al.
Database Crossfire, Beilstein BRN, XP002029003 & Justus Leibig Ann. Chem., Bd. 693, 1996, Seiten 134–157, Grell & Machleidt.
Database Crossfire, Beilstein BRN 5510882, XP002029004, & Chem. Lett., 1988, Seiten 1987–1990, Kubota, et al.
A.L. Henne, et al., The Alkaline Condensation of Fluorinated Esters with Esters and Ketones[1], The Journal of the American Chemical Society, vol. 69, pp. 1819–1820, (Jul., 1947).

T. Kitazume, et al., A microbially–based approach for the synthesis of chiral secondary alcohols bearing the difluoromethyl or chlorodifluoromethyl group, Journal of Fluorine Chemistry, 56, pp. 271–284, (1992).

A. Thenappan, et al., Acylation of Fluorocarbethoxy–Substituted Ylids: A Simple and General Route to α–Fluoro β–Keto Esters[1], J. Org. Chem., vol. 56, No. 1, pp. 273–277, (1991).

The Journal of the American Chemical Society, 72, p. 3289, (1950).

*Primary Examiner*—Amelia Owens
*Attorney, Agent, or Firm*—Sprung Kramer Schaefer & Briscoe

[57] ABSTRACT

The invention relates to novel 3,3-dioxy-4,4,4-trifluorobutyric acid derivatives of the formula (I)

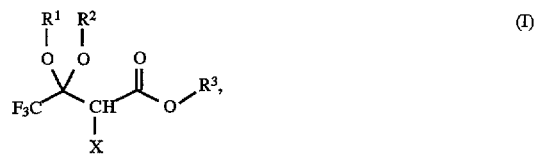

in which $R^1$ and $R^2$ independently of one another represent $C_1$–$C_{10}$-alkyl, or represent cyclohexyl, or represent optionally substituted $C_6$–$C_{10}$-aryl or $C_7$–$C_{14}$-arylalkyl, or $R^1$ and $R^2$ together represent $C_2$–$C_4$-alkylene which is optionally mono- or disubstituted by methyl, or optionally substituted ortho-arylene, $R^3$ represents hydrogen or $C_1$–$C_{10}$-alkyl, or represents cycloalkyl, or represents optionally substituted $C_6$–$C_{10}$-aryl or $C_7$–$C_{14}$-arylalkyl, and X represents hydrogen, fluorine, chlorine or bromine, excluding methyl 4,4,4-trifluoro-3,3-dimethoxybutyrate, 4,4,4-trifluoro-3,3-dimethoxybutyric acid, ethyl 4,4,4-trifluoro-3,3-diethoxybutyrate, ethyl 4,4,4-trifluoro-3,3-ethylenedioxybutyrate and 4,4,4-trifluoro-3,3-ethylenedioxybutyric acid, a process for their preparation and for the preparation of further 3,3-dioxy-4,4,4-trifluorobutyric acid derivatives, as well as novel intermediates and processes for their preparation.

10 Claims, No Drawings

3,3-DIOXY-4,4,4-TRIFLUOROBUTYRIC ACID DERIVATIVES

The invention relates to novel 3,3-dioxy-4,4,4-trifluorobutyric acid derivatives, a process for their preparation and for the preparation of other 3,3-dioxy-4,4,4-trifluorobutyric acid derivatives, and novel intermediates and processes for their preparation.

It is already known from DE-OS 4025188 and J. Am. Chem. Soc. 72, 3289 (1950) that 4,4,4-trifluoroacetoacetates or 2-chloro-4,4,4-trifluoroacetoacetates can be decarboxylated under acid conditions to give 1,1,1-trifluoroacetone or 3-chloro-1,1,1-trifluoroacetone. 1,1,1-Trifluoroacetone and 1,1,1-trifluoro-3-halogenoacetones are important units for the preparation of biologically active compounds (cf. EP-625 516 A1, EP-491 137 A2).

Novel compounds of the formula (I)

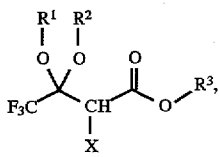
(I)

in which
- $R^1$ and $R^2$ independently of one another represent $C_1$–$C_{10}$-alkyl, in particular methyl ethyl, n-propyl, isopropyl, n-butyl, isobutyl, sec-butyl or tert-butyl, or represent cyclohexyl, or represent optionally substituted $C_6$–$C_{10}$-aryl or $C_7$–$C_{14}$-arylalkyl, or
- $R^1$ and $R^2$ together represent $C_2$–$C_4$-alkylene which is optionally mono- or disubstituted by methyl, or optionally substituted ortho-arylene,
- $R^3$ represents hydrogen, $C_1$–$C_{10}$-alkyl, in particular, methyl, ethyl, n-propyl, isopropyl, n-butyl, isobutyl, sec-butyl, or tert-butyl, or represents cyclohexyl, or represents optionally substituted $C_6$–$C_{10}$-aryl or $C_7$–$C_{14}$-arylalkyl, and
- X represents hydrogen, fluorine, chlorine or bromine, excluding methyl 4,4,4-trifluoro-3,3-dimethoxybutyrate, 4,4,4-trifluoro-3,3-dimethoxybutyric acid, ethyl 4,4,4-trifluoro-3,3-diethoxybutyrate, ethyl 4,4,4-trifluoro-3,3-ethylenedioxybutyrate and 4,4,4-trifluoro-3,3-ethylenedioxybutyric acid, preparation of which in a fundamentally different manner is known, have been found.

Compounds of the formula (I') are referred to below if the novel compounds of the formula (I) together with the abovementioned known compounds are meant.

The compounds of the formula (I) in which $R^3 \ne$ hydrogen can be hydrolyzed by the action of a base, for example by aqueous alkali metal or alkaline earth metal hydroxides or carbonates, and subsequent acidification to give the acids, i.e. compounds of the formula (I) in which $R^3$=hydrogen.

The compounds of the formula (I) can furthermore be reacted by the action of aqueous mineral acids at temperatures of, for example, 50° to 200° C., preferably between 90° and 150° C., to give the known 1,1,1-trifluoroacetones of the formula (II)

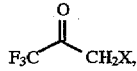
(II)

in which
X has the meaning given in the case of formula (I).

As mentioned above, these are interesting units for syntheses of heterocyclic compounds.

The compounds of the formula (I) can be converted by the action of Lewis acids, for example boron tribromide, into the corresponding 4,4,4-trifluoroacetoacetate derivatives of the formula (III)

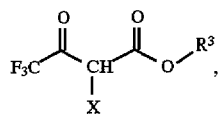
(III)

in which
$R^3$ and X have the meaning given in the case of formula (I).

These compounds are important intermediate products for fungicides (EP-371 950 A2).

The preparation of 4,4,4-trifluoroacetoacetates optionally halogenated in the 2-position by condensation of esters of optionally halogenated acetic acids or phosphorylides thereof with trifluoroacetates and, where appropriate, subsequent chlorination or bromination is described in the literature (cf., for example, J. Org. Chem. 56, 273 (1991); J. Fluorine Chem. 56, 271 (1992); J. Am. Chem. Soc. 69, 1819 (1947)). There are two essential disadvantages in carrying out the ester condensation, which thus also have an effect on the best synthesis route to date to the 1,1,1-trifluoroacetones. On the one hand, the trifluoroacetic acid esters required are not readily accessible and are therefore relatively expensive. On the other hand, if industrially accessible bases are used, such as, for example, sodium methylate or ethylate, only moderate yields are achieved. If higher yields are desired, bases which are expensive and, in particular, are difficult to handle industrially, such as sodium hydride or lithium diisopropylamide, must be used.

These disadvantages can be overcome by the compounds of the formula (I), which are readily accessible by the process described below.

It has furthermore been found that the compounds of the formula (I') can be prepared in a process (A) which comprises reacting the novel compounds of the formula (IV) or (V),

(IV)

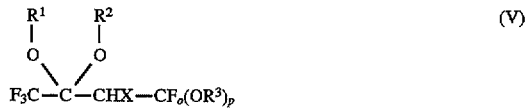
(V)

in which
- $R^1$ and $R^2$ independently of one another represent $C_1$–$C_{10}$-alkyl, in particular methyl, ethyl, n-propyl, isopropyl, n-butyl, isobutyl, sec-butyl or tert-butyl, or represent cyclohexyl, or represent optionally substituted $C_6$–$C_{10}$-aryl or $C_7$–$C_{14}$-arylalkyl, or
- $R^1$ and $R^2$ together represent $C_2$–$C_4$-alkylene which is optionally mono- or disubstituted by methyl, or optionally substituted ortho-arylene,
- $R^3$ represents hydrogen, $C_1$–$C_{10}$-alkyl, in particular methyl, ethyl, n-propyl, isopropyl, n-butyl, isobutyl, sec-butyl or tert-butyl, or represents cyclohexyl, or represents optionally substituted $C_6$–$C_{10}$-aryl or $C_7$–$C_{14}$-arylalkyl, and
- X represents hydrogen, fluorine, chlorine or bromine,
- n and o independently of one another represent the numbers 0, 1 or 2, m represents the numbers 0, 1 or 2, where n+m=2, and p represents 1, 2 or 3, where o+p=3, with a hydroxy compound of the formula (VI)

    (VI)

in which

R³ has the meaning given in the case of the formulae (IV) and (V), in the presence of a proton donor.

It has furthermore been found that the novel intermediate products of the formula (IV) or (V) can be prepared in a process (B) which comprises reacting dioxyhexafluorobutanes of the formula (VII)

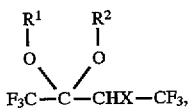    (VII)

in which

R¹, R² and X have the meanings given in the case of formula (I'), some of which are novel, with hydroxy compounds of the formula (VI) in the presence of an acid-binding agent.

This is surprising, because it is stated in J. Indian Chem. Soc. 30, 809 (1953) that in the reaction of 1,1,1,4,4,4-hexafluoro-2,3-dichloro-2-butene with methanolic KOH, in addition to 1,1,1,4,4,4-hexafluoro-3-chloro-2,2-dimethoxy butene, which is a compound of the formula (VII), 1,4,4,4-tetrafluoro-3-chloro-1,1,2-trimethoxybutane is obtained, this becoming the preferential product when the temperature is increased.

The compounds of the formula (VII) are novel, excluding 1,1,1,4,4,4-hexafluoro-2,2 -dimethoxy-3-chlorobutane, 1,1, 1,4,4,4-hexafluoro-2,2-diethoxy-3-chlorobutane, 1,1,1,4,4, 4-hexafluoro-2,2-ethylenedioxy-3-chlorobutane and 1,1,1,2, 4,4,4-heptafluoro-2,2-ethylenedioxybutane.

It has furthermore been found that the compounds of the formula (VII) can be prepared in a process (C) which comprises reacting, in a first step, hexafluorobutenes of the formula (VIII)

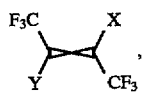    (VIII)

in which

X has the meaning given in the case of formula (I'),

Y represents fluorine, chlorine or bromine and the crossed double bond represents the E and/or Z form, with alcohols of the formulae (IX) and (X)

    (IX)

    (X), in which

R¹ and R² have the meaning given in the case of formula (I'), in the presence of an acid-binding agent and, if appropriate, in a second step, reacting the product with another alcohol of the formula (X) in the presence of an acid-binding agent.

In a preferred embodiment of process (A), compounds of the formula (I) are obtained by adding an acid to the reaction mixture from processes (B).

In a preferred embodiment of process (B), compounds of the formula (IV) or (V) are obtained starting from hexafluorobutenes of the formula (VIII) by choosing the reaction conditions in process (C) such that the compound of the formula (VII) initially formed is further reacted directly.

In a special embodiment, all three processes are combined in the abovementioned sense, so that hexafluorobutenes of the formula (VIII) are reacted "in one pot" to give specific 3,3-dioxy-4,4,4-trifluorobutyric acid derivatives of the formula (I), in which R¹, R² and R³ each represent an identical radical. This particularly simple and inexpensive process is advantageous in particular in respect of the use of the compounds of the formula (I) for the preparation of the trifluoroacetones of the formula (II) and the trifluoroacetoacetates of the formula (III).

Depending on the nature of the substituents, the compounds of the formula (I), (III), (IV), (V) and (VII) can also be present as geometric and/or optical isomers or isomer mixtures of varying composition, which can be separated, if appropriate, in the customary manner. The present invention relates both to the pure isomers and to the isomer mixtures and their preparation and use.

The general formula (I) provides a definition of the novel 3,3-dioxy-4,4,4-trifluorobutyric acid derivatives.

R¹ and R² independently of one another preferably represent $C_1$-$C_6$-alkyl, in particular methyl, ethyl, n-propyl, isopropyl, n-butyl, isobutyl, sec-butyl or tert-butyl, or represent cyclohexyl, or represent optionally halogen-, nitro-, cyano-, $C_1$-$C_4$-alkyl-, trifluoromethyl-, $C_1$-$C_4$-alkoxy-, trifluoromethoxy-, difluoromethoxy- or amino-substituted phenyl, naphthyl, benzyl or phenethyl.

R¹ and R² together preferably also represent $C_2$-$C_4$-alkylene, in particular ethylene, which is optionally mono- or disubstituted by methyl, or represent optionally halogen-, nitro-, cyano-, $C_1$-$C_4$-alkyl-, trifluoromethyl-, $C_1$-$C_4$-alkoxy-, trifluoromethoxy-, difluoromethoxy- or amino-substituted ortho-phenylene, o-naphthylene or o-anthrylene.

R³ preferably represents hydrogen, $C_1$-$C_6$-alkyl, in particular methyl, ethyl, n-propyl, isopropyl, n-butyl, isobutyl, sec-butyl or tert-butyl, or represents cyclohexyl or optionally halogen-, nitro-, cyano-, $C_1$-$C_4$-alkyl-, trifluoromethyl-, $C_1$-$C_4$-alkoxy-, trifluoromethoxy-, difluoromethoxy- or amino-substituted phenyl, naphthyl, benzyl or phenethyl.

Methyl 4,4,4-trifluoro-3,3-dimethoxybutyrate, 4,4,4-trifluoro-3,3-dimethoxybutyric acid, ethyl 4,4,4-trifluoro-3, 3-diethoxybutyrate, ethyl 4,4,4-trifluoro-3,3-ethylenedioxybutyrate and 4,4,4-trifluoro-3,3-ethylenedioxybutyric acid are excluded from the preferred range.

R¹ and R² independently of one another particularly preferably represent $C_1$-$C_6$-alkyl, in particular methyl, ethyl, n-propyl, isopropyl, n-butyl, isobutyl, sec-butyl or tert-butyl, or represent cyclohexyl, or represent optionally fluorine-, chlorine-, bromine-, nitro-, cyano-, $C_1$-$C_4$-alkyl-, trifluoromethyl-, $C_1C_4$-alkoxy-, trifluoromethoxy-, difluoromethoxy- or amino-substituted phenyl, naphthyl or benzyl.

R¹ and R² together also particularly preferably represent $C_2$-$C_3$-alkylene, in particular ethylene, which is optionally mono- or disubstituted by methyl, or represent optionally fluorine-, chlorine-, bromine-, nitro-, cyano-, $C_1$-$C_4$-alkyl-, trifluoromethyl-, $C_1$-$C_4$-alkoxy-, trifluoromethoxy-, difluoromethoxy- or amino-substituted ortho-phenylene, or o-naphthylene.

Methyl 4,4,4-trifluoro-3,3 -dimethoxybutyrate, 4,4,4-trifluoro-3,3 -dimethoxybutyric acid, ethyl 4,4,4-trifluoro-3, 3-diethoxybutyrate, ethyl, 4,4,4-trifluoro-3,3-ethylenedioxybutyrate and 4,4,4-trifluoro-3,3-ethylenedioxybutyric acid are excluded from the particularly preferred range.

$R^1$ and $R^2$ independently of one another especially preferably represent methyl, ethyl, n-propyl, isopropyl, n-butyl, isobutyl, sec-butyl or tert-butyl, or represent cyclohexyl, or represent optionally fluorine-, chlorine-, bromine-, nitro-, cyano-, methyl-, ethyl-, propyl-, isopropyl-, trifluoromethyl-, methoxy-, ethoxy-, trifluoromethoxy-, difluoromethoxy- or amino-substituted phenyl or benzyl.

$R^1$ and $R^2$ together also especially preferably represent ethylene, 1,2-propylene, 1,3-propylene or 2,4-butylene, or represent optionally fluorine-, chlorine-, bromine-, nitro-, cyano-, methyl-, ethyl-, propyl-, isopropyl-, trifluoromethyl-, methoxy-, ethoxy-, trifluoromethoxy-, difluoromethoxy- or amino-substituted ortho-phenylene, or o-naphthylene.

$R^3$ especially preferably represents hydrogen, methyl, ethyl, n-propyl, isopropyl, n-butyl, isobutyl, sec-butyl or tert-butyl, or represents cyclohexyl, or represents optionally fluorine-, chlorine-, bromine-, nitro-, cyano-, methyl-, ethyl-, propyl-, isopropyl-, trifluoromethyl-, methoxy-, ethoxy-, trifluoromethoxy-, difluoromethoxy- or amino-substituted phenyl or benzyl.

Methyl 4,4,4-trifluoro-3,3-dimethoxybutyrate, 4,4,4-trifluoro-3,3-dimethoxybutyric acid, ethyl 4,4,4-trifluoro-3,3-diethoxybutyrate, ethyl 4,4,4-trifluoro-3,3-ethylenedioxybutyrate and 4,4,4-trifluoro-3,3-ethylenedioxybutyric acid are excluded from the especially preferred range.

The abovementioned definitions of radicals or explanations given generally or in preferred ranges can be combined as desired with one another, that is to say also between the particular ranges and preferred ranges. They apply accordingly to the end products as well as to the precursors and intermediate products.

The compounds of the formula (I) in which a combination of the meanings given above as preferred (preferably) is present are preferred according to the invention.

The compounds of the formula (I) in which a combination of the meanings given above as particularly preferred is present are particularly preferred according to the invention.

The compounds of the formula (I) in which a combination of the meanings given above as especially preferred is present are especially preferred according to the invention.

Saturated or unsaturated hydrocarbon radicals, such as alkyl or alkenyl, also in combination with heteroatoms, such as, for example, in alkoxy, can be in each case straight-chain or branched, where possible.

Optionally substituted radicals can be mono- or polysubstituted, it being possible for the substituents to be identical or different and, where possible, to be present once to three times in the case of polysubstitutions.

If, for example, 1,4,4,4-tetrafluoro-2-chloro-1-ethoxy-3,3-dimethoxy-1-butene and ethanol are used as starting substances, the course of the reaction of process (A) according to the invention can be represented by way of example by the following equation:

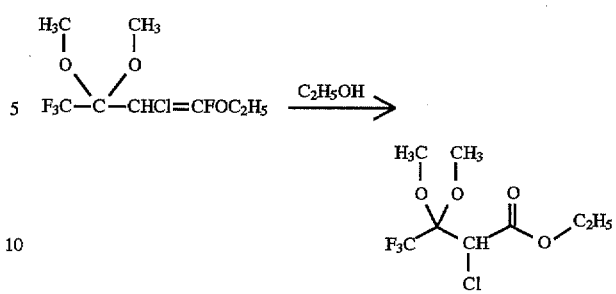

If, for example, 1,1,1,3,4,4,4-heptafluoro-2,2-diethoxybutane and methanol are used as starting substances, the course of the reaction of process (B) according to the invention can be represented, for example, by the following equation:

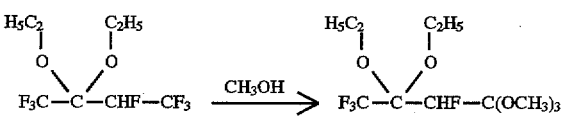

If, for example, E-1,1,1,2,4,4,4-heptafluoro-3-chloro-2-butene and ethanediol are used as starting substances, the course of the reaction of process (C) according to the invention can be represented, for example, by the following equation:

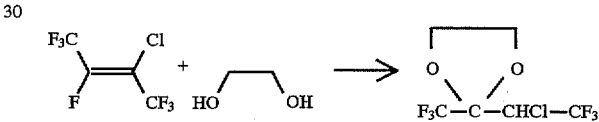

The formulae (IV) and (V) provide general definitions of the ketals required for carrying out process (A) according to the invention. In these formulae, $R^1$, $R^2$, $R^3$ and X preferably represent those radicals which have already been mentioned as preferred substituents in connection with the description of the 3,3-dioxy-4,4,4-trifluorobutyric acid derivatives of the formula (I). The indices n, m, o and p are also preferably as mentioned above. Both pure compounds of the formula (IV) or of the formula (V), mixtures of different compounds of the formula (IV) with the same radicals but different m and n in themselves and various compounds of the formula (V) with the same radicals but different o and p, as well as mixtures of the compounds of the formulae (IV) and (V) with the same radicals, can be employed in any desired ratio relative to one another.

The compounds of the formulae (IV) and (V) are novel and can be prepared, for example, by process (B).

The formula (VI) provides a general definition of the hydroxy compounds required for carrying out process (A) according to the invention. In this formula, $R^3$ preferably represents those radicals which have already been mentioned as preferred substituents in connection with the description of the 3,3-dioxy-4,4,4-trifluorobutyric acid derivatives of the formula (I).

The compounds of the formula (VI) are generally known chemical compounds.

Process (A) according to the invention is carried out in the presence of a proton donor. Possible proton donors are all the inorganic and organic proton acids and also Lewis acids (because of the presence of a hydroxy compound), as well as all the polymeric acids. These include, for example, hydrogen chloride, sulfuric acid, phosphoric acid, formic acid, acetic acid, trifluoroacetic acid, methanesulfonic acid, trifluoromethanesulfonic acid, toluenesulfonic acid, boron trifluoride (also as the etherate), boron tribromide, aluminum trichloride, zinc chloride, iron(III) chloride, antimony pentachloride, acidic ion exchangers, acidic aluminas and acidic silica gel.

Process (A) is preferably carded out in the presence of a diluent. Possible diluents for this process are, particularly preferably, water and/or an excess of the hydroxy compound (VI), and in addition organic solvents and any desired mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro- or trichloroethane or tetrachloroethylene; ethers, such as diethyl, diisopropyl, methyl t-butyl or methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric acid triamide; N-oxides, such as N-methylmorpholine N-oxide; esters, such as methyl, ethyl or butyl acetate; sulfoxides, such as dimethyl sulfoxide; and sulfones, such as sulfolane.

The reaction temperatures can be varied within a substantial range in carrying out process (A) according to the invention. The reaction is in general carried out at temperatures between 0° C. and +250° C., preferably at temperatures between +20° C. and 150° C.

Process (A) is usually carried out under normal pressure. However, it is also possible to carry out the process under increased or reduced pressure.

For carrying out process (A) according to the invention, for example, 0.8 to 100 mol, preferably 1 to 20 mol, of hydroxy compound of the formula (VI) and 0.1 to 100 mol, preferably 1 to 50 mol, of proton donor are employed per mole of ketal of the formula (VI) and/or (V).

The reaction is carried out and the reaction products are worked up and isolated by generally customary, known processes (cf. also the examples).

The formula (VII) provides a general definition of the dioxyhexafluorobutanes required for carrying out process (B) according to the invention. In this formula, $R^1$, $R^2$ and X preferably represent those radicals which have already been mentioned as preferred substituents in connection with the description of the 3,3-dioxy-4,4,4-trifluorobutyric acid derivatives of the formula (I).

The compounds of the formula (VII) are novel, apart from the three abovementioned exceptions, and can be prepared, for example, by process (C).

The formula (VI) provides a general definition of the hydroxy compounds required for carrying out process (B) according to the invention, which are described in the case of process (A), Process (B) according to the invention is carried out in the presence of a suitable acid acceptor. Possible acid acceptors are all customary inorganic and organic bases. These include, preferably, alkaline earth metal and alkali metal hydrides, hydroxides, amides, alcoholates, acetates, carbonates and bicarbonates, such as, for example, sodium hydride, sodium amide, sodium methylate, sodium ethylate, potassium tert-butylate, sodium hydroxide, potassium and ammonium hydroxide, sodium, potassium, calcium and ammonium acetate, sodium, potassium and ammonium carbonate and sodium bicarbonate and potassium bicarbonate, as well as tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) and diazabicycloundecene (DBU). An alkali metal salt of the particular hydroxy compound of the formula (VI) employed is particularly preferably employed.

If appropriate, process (B) can be carried out in the presence of a diluent. Possible diluents for this process are water, an excess of the hydroxy compound (VI), organic solvents and any desired mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro- or trichloroethane or tetrachloroethylene; ethers, such as diethyl, diisopropyl, methyl-t-butyl or methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric acid triamide; N-oxides, such as N-methylmorpholine N-oxide; esters, such as methyl, ethyl, or butyl acetate; sulfoxides, such as dimethyl sulfoxide; and sulfones, such as sulfolane.

If appropriate, process (B) according to the invention may be carried out in the presence of a suitable phase transfer catalyst. Examples of such catalysts which may be mentioned are: tetrabutylammonium iodide, bromide and chloride, tributylmethylphosphonium bromide, trimethyl-$C_{13}$–$C_{15}$-alkylammonium chloride and bromide, dibenzyldimethylammonium methyl-sulfate, dimethyl-$C_{12}$–$C_{14}$-alkylbenzylammonium chloride, 15-crown-5, 18-crown-6 or tris-[2-(2-methoxyethoxy)-ethyl]-amine.

The reaction temperatures can be varied within a substantial range in carrying out process (B) according to the invention. The reaction is in general carried out at temperatures between 0° C. and +250° C., preferably at temperatures between +20° C. and 150° C.

Process (B) is usually carried out under normal pressure. However, it is also possible to carry out the process under increased or reduced pressure.

For carrying out process (B) according to the invention, for example, 1 to 1000 mol, preferably 1.5 to 500 mol, of hydroxy compound of the formula (VI) and 1 to 100 mol, preferably 1.2 to 20 mol, of acid acceptor are employed per mole of dioxyhexafluorobutane of the formula (VII).

The reaction is carried out and the reaction products are worked up and isolated by generally customary, known processes (cf. also the examples).

The formula (VIII) provides a general definition of the hexafluorobutenes required for carrying out process (C) according to the invention. In this formula, Y preferably represents fluorine or chlorine.

The compounds of the formula (VIII) are known from EP-315 783 A1 and in some cases are commercially obtainable.

The formula (IX) and, where appropriate, the formula (X) provide general definitions of the alcohols required for carrying out process (C) according to the invention. In these formulae, $R^1$ and $R^2$ preferably represent those radicals which have already been mentioned as preferred substituents in connection with the description of the 3,3-dioxy-4,4,4-trifluorobutyric acid derivatives of the formula (I). If monofunctional alcohols are employed, an alcohol of the formula (IX) can be employed by itself or as a mixture with another of the formula (X). Preferably, only one alcohol is used, and in this case formula (IX) is formally identical to formula (X). Diols can also be employed, in which case $R^1$ and $R^2$ together represent one of the abovementioned bifunctional radicals.

The compounds of the formulae (IX) and (X) are generally known chemical compounds.

Process (C) according to the invention is carried out in the presence of a suitable acid acceptor. Possible acid acceptors are all the customary inorganic and organic bases. These include, preferably, alkaline earth metal and alkali metal hydrides, hydroxides, amides, alcoholates, acetates, carbonates and bicarbonates, such as, for example, sodium hydride, sodium amide, sodium methylate, sodium ethylate, potassium tert-butylate, sodium hydroxide, potassium and ammonium hydroxide, sodium, potassium, calcium and ammonium acetate, sodium, potassium and ammonium carbonate and sodium bicarbonate and potassium bicarbonate, as well as tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) and diazabicycloundecene (DBU). An alkali metal salt of the particular hydroxy compound of the formula (VI) employed is particularly preferably employed.

If appropriate, process (C) can be carried out in the presence of a diluent. Possible diluents for this process are water, organic solvents and any desired mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro- or trichloroethane or tetrachloroethylene; ethers, such as diethyl, diisopropyl, methyl-t-butyl or methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylformamide, N,N-dimethylacetamide, N-methylformanilide, N-methylpyrrolidone or hexamethylphosphoric acid triamide; N-oxides, such as N-methylmorpholine N-oxide; esters, such as methyl, ethyl, or butyl acetate; sulfoxides, such as dimethyl sulfoxide; and sulfones, such as sulfolane.

If appropriate, process (C) according to the invention can be carried out in the presence of a suitable phase transfer catalyst. For example, the catalysts listed in the case of process (B) can be used.

The reaction temperatures can be varied within a substantial range in carrying out process (C) according to the invention. The reaction is in general carried out at temperatures between −80° C. and +150° C., preferably at temperatures between 0° C. and 120° C.

Process (C) is usually carried out under normal pressure. However, it is also possible to carry out the process under increased or reduced pressure.

For carrying out process (C) according to the invention, for example, in each case 1 to 100 mol, preferably 1.5 to 50 mol, of alcohol(s) of the formulae (IX) and (X) and 1 to 100 mol, preferably 1.2 to 20 mol, of acid acceptor are added per mole of hexafluorobutene of the formula (VIII).

The reaction is carried out and the reaction products are worked up and isolated by generally customary, known methods (cf. also the examples).

EXAMPLES

Example 1

2-Methyl chloro-4,4,4-trifluoro-3,3-dimethoxybutanecarboxylate 618 g of a 30% strength solution of sodium methylate in methanol were added dropwise to 200 g of 2,3-dichloro-1,1,1,4,4,4-hexafluorobut-2-ene and the reaction mixture was heated under reflux for 16 hours. It was cooled to room temperature and 150 ml of 50% strength sulfuric acid were added. The mixture was then stirred at the reflux temperature again for 3 hours. Water was added and the mixture was extracted with methylene chloride. After drying over sodium sulfate and removal of the solvent, the residue was distilled in vacuo (boiling point: 85° C./10 mbar).

Yield: 178 g of methyl 2-chloro-4,4,4-trifluoro-3,3-dimethoxybutanecarboxylate. $^1$H-NMR (CDCl$_3$)δ[ppm]: 3.5 (s, 3H); 3.6 (s, 3H); 3.83 (s, 3H); 4.68 (s, 1H) $^{19}$F-NMR (CDCl$_3$)δ[ppm]: −76.18 (s)

Example 2

Reaction of 2,3-dichloro-1,1,1,4,4,4-hexafluorobut-2-ene with sodium methylate 1280 g of a 30% strength solution of sodium methylate in methanol were added dropwise to 400 g of 2,3-dichloro-1,1,4,4,4-hexafluorobut-2-ene in 200 ml of methanol and the mixture was heated under reflux for 10 hours. The salts which had precipitated out were filtered off and the methanol was removed in vacuo. Water was added to the residue and the mixture was extracted with methyl t-butyl ether. After drying of the organic phase with sodium sulfate and removal of the solvent, 452 g of a mixture of 38% of 1,1,1,4,4-pentafluoro-3-chloro-2,2,4-trimethoxybutane, 23% of 2-chloro-1,4,4,4-tetrafluoro-1,3,3-trimethoxy-but-1 -ene and 31% of methyl 2-chloro-4,4,4-trifluoro-3,3-dimethoxybutanecarboxylate were obtained.

Example 3

Methyl 2-chloro-4,4,4-trifluoro-3,3-dimethoxybutanecarboxylate 150 ml of 50% strength sulfuric acid were added to 300 g of the reaction mixture from Example 2 in 800 ml of methanol and the mixture was stirred under reflux for 5 hours. The solvent was largely removed on a rotary evaporator and the residue was poured onto water. The mixture was extracted with methylene chloride and dried over sodium sulfate and the solvent was removed in vacuo. After distillation (boiling point: 85° C./10 mbar), 271 g of methyl 2-chloro-4,4,4-trifluoro-3,3-dimethoxybutanecarboxylate were obtained.

Example 4

Methyl 2-chloro-4,4,4-trifluoro-3,3-dimethoxybutanecarboxylate 500 ml of 50% strength sulfuric acid were added to 100 g of the reaction mixture from Example 2 and the mixture was stirred at 80° C. for 5 hours. It was extracted with methylene chloride and dried over sodium sulfate and the solvent was removed in vacuo. After distillation, 73 g of methyl 2-chloro-4,4,4-trifluoro-3,3-dimethoxybutanecarboxylate were obtained.

Example 5

5 2-Chloro-1,4,4,4-tetrafluoro-1,3,3-triethoxybut-1-ene 1400 ml of a 20% strength solution of sodium ethylate in ethanol were added dropwise to 233 g of 2,3-dichloro-1,1,1,4,4,4-hexafluorobut-2-ene in 300 ml of ethanol and the mixture was heated under reflux for 2 hours. The salts which had precipitated out were filtered off and the ethanol was removed in vacuo. Water was added to the residue and the mixture was extracted with methyl t-butyl ether. After drying of the organic phase with sodium sulfate and removal of the solvent, 229 g of 2-chloro-1,4,4,4-tetrafluoro-1,3,3-triethoxy-but-1-ene were obtained.

$^1$H-NMR (CDCl$_3$)δ[ppm]: 1.3 (m, 9H); 3.7 (m, 6H); 4.2 (m, 2H) $^{19}$F-NMR (CDCl$_3$)δ[ppm]: −78.2 (d); −81 (q)

Example 6

Ethyl 2-chloro-4,4,4-trifluoro-3,3-diethoxybutanecarboxylate 100 ml of 50% strength sulfuric acid were added to 100 g of 2-chloro-1,4,4,4-tetrafluoro-1,3,3-triethoxy-but-1-ene in 200 ml of ethanol and the mixture was stirred under reflux for 3 hours. It was poured onto water and extracted with methylene chloride. The organic phase was dried over sodium sulfate and the solvent was removed in vacuo. The residue was distilled in vacuo. 79 g of ethyl 2-chloro-4,4,4-trifluoro-3,3-diethoxybutanecarboxylate of boiling point 48° C. under 0.2 mbar were isolated.

$^1$H-NMR (CDCl$_3$)δ[ppm]: 1.3 (m, 9H); 3.67 (m, 1H); 3.72 (m, 1H); 3.82 (m, 1H); 4.09 (m, 1H); 4.25 (m, 2H); 4.63 (s, 1H) $^{19}$F-NMR (CDCl$_3$)δ[ppm]: −76.95 (s)

Example 7

Ethyl 2-chloro-4,4,4-trifluoro-3,3-dimethoxybutanecarboxylate 265 g of a 20% strength solution of sodium ethylate in ethanol were added dropwise to 100 g of 2-chloro-1,1,1,4,4,4-hexafluoro-3,3-dimethoxy-butane in 50 ml of ethanol at room temperature. The reaction mixture was then stirred under reflux for 12 hours and cooled to room temperature, and 100 ml of 50% strength sulfuric acid were added dropwise. After the mixture had been refluxed again for 3 hours, it was poured onto water and extracted with methylene chloride and the organic phase was dried over sodium sulfate. After removal of the solvent, the residue was distilled in vacuo.

Yield: 82 g (boiling point: 89° C./14 mbar) $^1$H-NMR (CDCl$_3$)δ[ppm]: 1.3 (t, 3H); 3.5 (s, 3H); 3.58 (s, 3H); 4.28 (q, 2H); 4.62 (s, 1H) $^{19}$F-NMR (CDCl$_3$)δ[ppm]: −76.03 (s)

Example 8

2-Chloro-4,4,4-trifluoro-3,3-dimethoxybutanecarboxylic acid 32 g of sodium hydroxide were added to 50 g of 2-chloro-1,1,1,4,4,4-hexafluoro-3,3-dimethoxy-butane, 0.5 g of tetrabutylammonium bromide and 300 ml of water and the mixture was stirred at 100° C. for 12 hours. 50 ml of 50% strength sulfuric acid were added dropwise, while cooling, and the reaction mixture was then poured onto 100 ml of water. The mixture was extracted twice with 200 ml of methylene chloride and the combined organic phases were dried over sodium sulfate. After removal of the solvent in vacuo, 42 g of 2-chloro-4,4,4-trifluoro-3,3-dimethoxybutanecarboxylic acid were obtained.

$^1$H-NMR (CDCl$_3$)δ[ppm]: 3.52 (s, 3H); 3.59 (s, 3H); 4.68 (s, 1H); 9.5 (s, 1H) $^{19}$F-NMR (CDCl$_3$)δ[ppm]: −75.7 (s)

Example 9

2-Chloro-1,1,1,4,4,4-hexafluoro-3,3-ethylenedioxybutane 233 g of 2,3-dichloro-1,1,1,4,4,4-hexafluorobut-2-ene were added dropwise to 400 ml of toluene, 80 g of ethylene glycol and 80 g of 60% strength sodium hydride in mineral oil at room temperature. The reaction mixture was stirred at 40° C. for 5 hours and water was then added. The organic phase was separated off, the aqueous phase was extracted with methyl t-butyl ether and the combined organic phases were dried over sodium sulfate. After removal of the solvent and subsequent distillation in vacuo, 180 g of 2-chloro-1,1,1,4,4,4-hexafluoro-3,3-ethylenedioxybutane (boiling point: 48° C./16 mbar) were obtained.

$^1$H-NMR (CDCl$_3$)δ[ppm]: 4.28 (m, 4H); 4.5 (q, 1H) $^{19}$F-NMR (CDCl$_3$)δ[ppm]: −68.75 (m); −79.9 (q)

Example 10

Ethyl 2-chloro-4,4,4-trifluoro-3,3-ethylenedioxybutanecarboxylate 80 g of a 20% strength solution of sodium ethylate in ethanol were added to 30 g of 2-chloro-1,1,1,4,4,4-hexafluoro-3,3-ethylenedioxybutane in 30 ml of ethanol and the mixture was stirred under reflux for 10 hours. 100 ml of 50% strength sulfuric acid were then metered in and the mixture was stirred under reflux for 6 hour. It was poured onto ice and extracted with methylene chloride. After drying over sodium sulfate and removal of the solvent and subsequent distillation in vacuo, 24 g of ethyl 2-chloro-4,4,4-trifluoro-3,3-ethylenedioxybutanecarboxylate of boiling point 108° C./20 mbar were obtained.

$^1$H-NMR (CDCl$_3$)δ[ppm]: 1.3 (t, 3H); 4.28 (m, 6H), 4.62 (s, 1H) $^{19}$F-NMR (CDCl$_3$)δ[ppm]: −80.2 (s)

Example 11

1- Chloro-4,4,4-trifluoroacetone 250 g of methyl 2-chloro-4,4,4-trifluoro-3,3-dimethoxybutanecarboxylate were added dropwise to 400 ml of concentrated sulfuric acid at 140° C. in the course of 2 hours, and at the same time the product was distilled off. The distillate was then redistilled over a 10 cm Vigreux column. 122 g of 1-chloro-3,3,3-trifluoroacetone (yield 83%) of boiling point 73° C. were obtained.

I claim:

1. A compound of the formula (I)

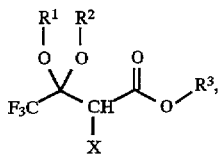

in which

R¹ and R² independently of one another represent $C_1$–$C_{10}$-alkyl, or represent cyclohexyl, or represent optionally substituted $C_6$–$C_{10}$-aryl or $C_7$–$C_{14}$-arylalkyl, or R¹ and R² together represent $C_2$–$C_4$-alkylene which is optionally mono- or disubstituted by methyl, or optionally substituted ortho-arylene, R³ represents hydrogen or $C_1$–$C_{10}$-alkyl, or represents cycloalkyl, or represents optionally substituted $C_6$–$C_{10}$-aryl or $C_7$–$C_{14}$-arylalkyl, and X represents hydrogen, fluorine, chlorine or bromine, excluding methyl 4,4,4-trifluoro-3,3-dimethoxybutyrate, 4,4,4-trifluoro-3,3-dimethoxybutyric acid, ethyl 4,4,4-trifluoro-3,3-diethoxybutyrate, ethyl 4,4,4-trifluoro-B,3-ethylenedioxybutyrate and 4,4,4-trifluoro-3,3-ethylenedioxybutyric acid.

2. A process for the preparation of 4,4,4-trifluoroacetoacetate derivatives of the formula

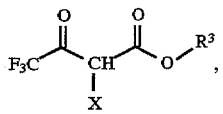

in which

R³ and X have the meaning given in claim 1, which comprises reacting the compound of claim 1 with a Lewis acid.

3. A process for the preparation of a compound of the formula

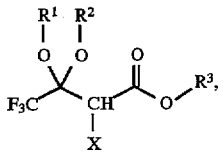

in which

R¹ and R² independently of one another represent $C_1$–$C_{10}$-alkyl, or represent cyclohexyl, or represent optionally substituted $C_6$–$C_{10}$-aryl or $C_7$–$C_{14}$-arylalkyl, or R¹ and R² together represent $C_2$–$C_4$-alkylene which is optionally mono- or disubstituted by methyl, or optionally substituted ortho-arylene, R³ represents hydrogen or $C_1$–$C_{10}$-alkyl, or represents cyclohexyl, or represents optionally substituted $C_6$–$C_{10}$-aryl or $C_7$–$C_{14}$-arylalkyl, and X represents hydrogen, fluorine, chlorine or bromine, which comprises reacting a compound of the formula (IV) or (V)

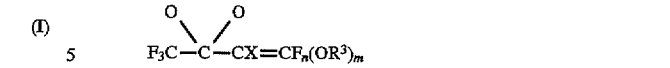

in which

R¹, R², R³ and X have the meaning given above in the case of formula (I') and n and o independently of one another represent the numbers 0, 1 or 2, m represents the numbers 0, 1 or 2, where n+m=2 and p represents 1, 2 or 3, where o+p=3, with a hydroxy compound of the formula (VI)

in which

R³ has the meaning given in the case of the formulae (IV) and (V), in the presence of a proton donor.

4. A process for the preparation of a compound of the formula (IV) or (V) given in claim 3, which comprises reacting a dioxyhexafluorobutane of the formula

in which

R¹, R² and X have the meanings given above in the case of formula (I'), with a hydroxy compound of the formula

in which

R³ has the meaning given in the case of formula (I') in claim 3, in the presence of an acid-binding agent.

5. A process for the preparation of a compound of the formula

in which

R¹, R² and X have the meaning given in the case of formula (I') in claim 3, which comprises reacting, in a first step, a hexafluorobutene of the formula

in which

X has the meaning given in the case of formula (I') in claim 3,

Y represents fluorine, chlorine or bromine and the crossed double bond represents the E and/or Z form, with an alcohol of the formula $$R^1\text{—OH} \qquad (IX)$$

or $$R^2\text{—OH} \qquad (X),$$

in which

R$^1$ and R$^2$ have the meaning given in the case of formula (I') in claim 3, in the presence of an acid-binding agent.

6. The process as claimed in claim 5, wherein, in a second step, the product is additionally reacted with another alcohol of the formula (X) in the presence of an acid-binding agent.

7. A process for the preparation of a 1,1,1-trifluoroacetone of the formula

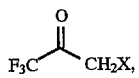

$$(II)$$

in which

X has the meaning given in claim 1, wherein the compound of claim 1 is reacted with a mineral acid.

8. A compound of the formula

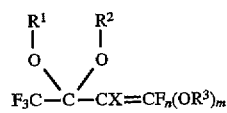

$$(IV)$$

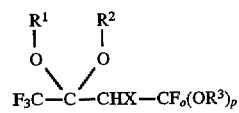

$$(V)$$

in which

R$^1$ and R$^2$ independently of one another represent C$_1$–C$_{10}$-alkyl, or represent cyclohexyl, or represent optionally substituted C$_6$–C$_{10}$-aryl or C$_7$–C$_{14}$-arylalkyl, or R$^1$ and R$^2$ together represent C$_2$–C$_4$-alkylene which is optionally mono- or disubstituted by methyl, or optionally substituted ortho-arylene, R$^3$ represents hydrogen or C$_1$–C$_{10}$-alkyl, or represents cycloalkyl, or represents optionally substituted C$_6$–C$_{10}$-aryl or C$_7$–C$_{14}$-arylalkyl, and X represents hydrogen, fluorine, chlorine or bromine, n and o independently of one another represent the numbers 0, 1 or 2, m represents the numbers 0, 1 or 2, where n+m=2 and p represents 1, 2 or 3, where o+p=3.

9. A compound of the formula

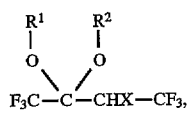

$$(VII)$$

in which

R$^1$, R$^2$ and X have the meaning given in claim 1, excluding 1,1,1,4,4,4-hexafluoro-2,2-dimethoxy-3-chlorobutane, 1,1,1,4,4,4-hexafluoro-2,2-diethoxy-3-chlorobutane, 1,1,1,4,4,4-hexafluoro-2,2-ethylenedioxy-3-chlorobutane and 1,1,1,2,4,4,4-heptafluoro-2,2-ethylenedioxy-butane.

10. A one-pot process for the preparation of a compound of the formula

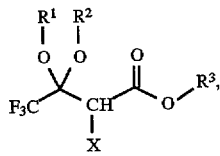

$$(I')$$

wherein R$^1$, R$^2$, R$^3$ and X have the meanings given in claim 3 and R$^1$, R$^2$, and R$^3$ are identical which comprises reacting, in a first step, a hexafluorobutene of the formula

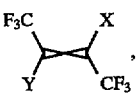

$$(VIII)$$

in which

X has the meaning given above,

Y represents fluorine, chlorine or bromine and the crossed double bond represents the E and/or Z form, with an alcohol of the formula $$R^1\text{—OH} \qquad (IX)$$

or $$R^2\text{—OH} \qquad (X),$$

in which

R$^1$ and R$^2$ have the meaning given above, in the presence of an acid-binding agent to form a dioxyhexafluorobutane of the formula

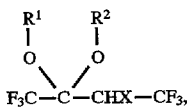

$$(VII)$$

in which

R$^1$, R$^2$ and X have the meaning given above, and then reacting said dioxyhexafluorobutane with a hydroxy compound of the formula $$R^3\text{—OH} \qquad (VI),$$

in which

R$^3$ has the meaning given above, in the presence of an acid-binding agent to form said compound of said formula (IV) or said formula (V) of claim 3, and further reacting with additional R$^3$OH in the presence of a proton donor.

* * * * *

UNITED STATES PATENT AND TRADEMARK OFFICE
CERTIFICATE OF CORRECTION

PATENT NO. : 5,739,394
DATED : April 14, 1998
INVENTOR(S) : Lui, Norbert

It is certified that error appears in the above-indentified patent and that said Letters Patent is hereby corrected as shown below:

Col. 13, line 28    Delete " ethyl 4,4,4-trifluoro-B,3- " and substitute -- ethyl 4,4,4-trifluoro-3,3- --

Signed and Sealed this

Twentieth Day of April, 1999

Attest:

Q. TODD DICKINSON

*Attesting Officer*    *Acting Commissioner of Patents and Trademarks*